(12) United States Patent
Jascob et al.

(10) Patent No.: US 8,320,991 B2
(45) Date of Patent: Nov. 27, 2012

(54) PORTABLE ELECTROMAGNETIC NAVIGATION SYSTEM

(75) Inventors: Bradley A. Jascob, Broomfield, CO (US); Vince J. Doerr, Boulder, CO (US); Paul Kessman, Lake Wood, CO (US); Orey G. Block, Westminster, CO (US); Jeffrey Swetnam, Superior, CO (US); John H. Dukesherer, Lakewood, CO (US)

(73) Assignee: Medtronic Navigation Inc., Louisville, CO (US)

( * ) Notice: Subject to any disclaimer, the term of this patent is extended or adjusted under 35 U.S.C. 154(b) by 988 days.

(21) Appl. No.: 11/607,762

(22) Filed: Dec. 1, 2006

(65) Prior Publication Data
US 2008/0132909 A1 Jun. 5, 2008

(51) Int. Cl.
*A61B 5/05* (2006.01)
(52) U.S. Cl. ......... 600/424; 600/420; 600/421; 600/422
(58) Field of Classification Search .................. 606/130; 600/409, 414, 415, 417, 420–422, 424, 426
See application file for complete search history.

(56) References Cited

U.S. PATENT DOCUMENTS

| | | | | |
|---|---|---|---|---|
| 6,427,079 B1 * | 7/2002 | Schneider et al. | ............ | 600/424 |
| 2002/0151777 A1 | 10/2002 | Hynynen et al. | | |
| 2003/0070236 A1 * | 4/2003 | Barker | .............................. | 5/658 |
| 2004/0085981 A1 * | 5/2004 | Lee et al. | ....................... | 370/412 |
| 2004/0250819 A1 | 12/2004 | Blair et al. | | |
| 2006/0036157 A1 * | 2/2006 | Tumer | ............................ | 600/411 |
| 2007/0035818 A1 * | 2/2007 | Bahatt et al. | .................. | 359/366 |

FOREIGN PATENT DOCUMENTS
EP 1571581 9/2005

OTHER PUBLICATIONS

International Preliminary Report on Patentability for PCT/US2007/024555 mailed Feb. 26, 2009 claiming priority to U.S. Appl. No. 11/607,762, filed Dec. 1, 2006.
Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).
International Search Report and Written Opinion mailed Apr. 28, 2008 for International Application No. PCT/US2007/024555.

* cited by examiner

*Primary Examiner* — Brian Casler
*Assistant Examiner* — Daniel Huntley
(74) *Attorney, Agent, or Firm* — Harness, Dickey

(57) ABSTRACT

A portable system can be provided that works with a surgical navigation system. The portable system can control a localizer to assist in the tracking of a tracking device. The portable system can be provided to be substantially carried by a single user form one location to another. Further, various digital control components can be provided to assist in miniaturization, robustness, and the like.

42 Claims, 5 Drawing Sheets

PORTABLE ELECTROMAGNETIC NAVIGATION SYSTEM

FIELD

The present teachings are directed to a surgical navigation system, and particularly to a portable surgical navigation system.

BACKGROUND

The statements in this section merely provide background information related to the present disclosure and may not constitute prior art.

An anatomy, such as a human anatomy, includes many portions that work in concert with one another. For various reasons, such as injury, disease, stress, and the like, many anatomical portions may become worn or need replacement or repair. Surgical procedures have been developed to assist in repairing or replacing various anatomical portions. These surgical procedures, however, often require generally invasive procedures to obtain access to the necessary portions of the anatomy to perform the procedure.

It is desired to provide a system to allow for imaging and viewing of an anatomical region while minimizing or reducing invasiveness of a procedure. For example, various imaging techniques have been developed to image portions of the anatomy. Nevertheless, to allow for performing a procedure on an anatomy, the overlying tissues may often be moved or removed to obtain access to the anatomical portions.

Various guiding systems, such as navigation systems, can be provided to allow for a virtual or image guided view of a patient (i.e., patient space) by viewing image data of a patient (i.e., image space). Navigation systems, however, generally require large storage, computational systems, and other large components. For example, large amplifiers are required to power the wire coils to create the navigation fields. Also, large power supplies are required to power the amplifiers and power the processors. Processors are also required in multiple components to process the navigation and image data. Therefore, providing a more portable and adaptable navigation system for use in an operating room (OR) is desired.

SUMMARY

A substantially mobile system that can be moved from one position to another or from one surgical operating theatre to another. This system can generally be moved by a single user in a substantially portable case. The case can be of a mass or volume that can be moved by a single user from one place to another. Further, the system can include durable or ruggedized components that are unaffected or minimally affected by shock, thermal change, or other environmental aspects. Further, digital systems can be provided to allow for substantial reduction in size and fast switching for various systems. Also, wireless communication systems can be provided to eliminate hard-wiring or clutter in certain situations. The system can also include a minimal number of small components that can be configured to be integrated into current operating room situations. The components can be positioned for ease of use and maneuverability in an operating room of the operating room staff.

According to various embodiments a navigation system for use in an operating theater to navigate a procedure relative to a patient is taught. The navigation system can include a tracking device including a coil to transmit a field, receive a field, or combinations thereof. A tracking array controller can be positioned within a container having a volume of about 32 cc to about 9850 cc and operable to be transported in a hand of a user and a digital amplifier associated with the tracking array controller. A tracking array can also be provided that includes at least three coils positioned relative to one another and each of the coils driven by the digital amplifier. The tracking array is operable to transmit a field, receive a field, or combinations thereof relative to the tracking device.

According to various embodiments a navigation system for use in an operating theater to navigate a procedure relative to a patient is taught. The system can include an imaging device to obtain image date of the patient and a surgical instrument to assist in performing a surgical procedure on the patient. A tracking device can be interconnected with the surgical instrument and a tracking system including a tracking array and a tracking array controller having a digital amplifier to amplify a signal to drive the tracking array can be provided to interact with the tracking device. A drive system to provide a drive current to the digital amplifier can also be included.

According to various embodiments a navigation system for use in an operating theatre to navigate a procedure relative to a patient is taught. A coil array having at least three coils operable to transmit a field, receive a field, or combinations thereof that is changed by at least one of a time differential, a time duplex, a frequency duplex, or combinations thereof is taught. An instrument can also be provided and a first tracking device can be associated with the instrument operable with the coil array to at least one of transmit a second field, receive the field of the array, or combinations thereof. A coil array controller can have a digital amplifier, a digital switch operable to switch each of the three coils according to the selected transmission type, and a power supply having a digital switch operable to provide an isolation between the tracking device or instrument and the patient.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
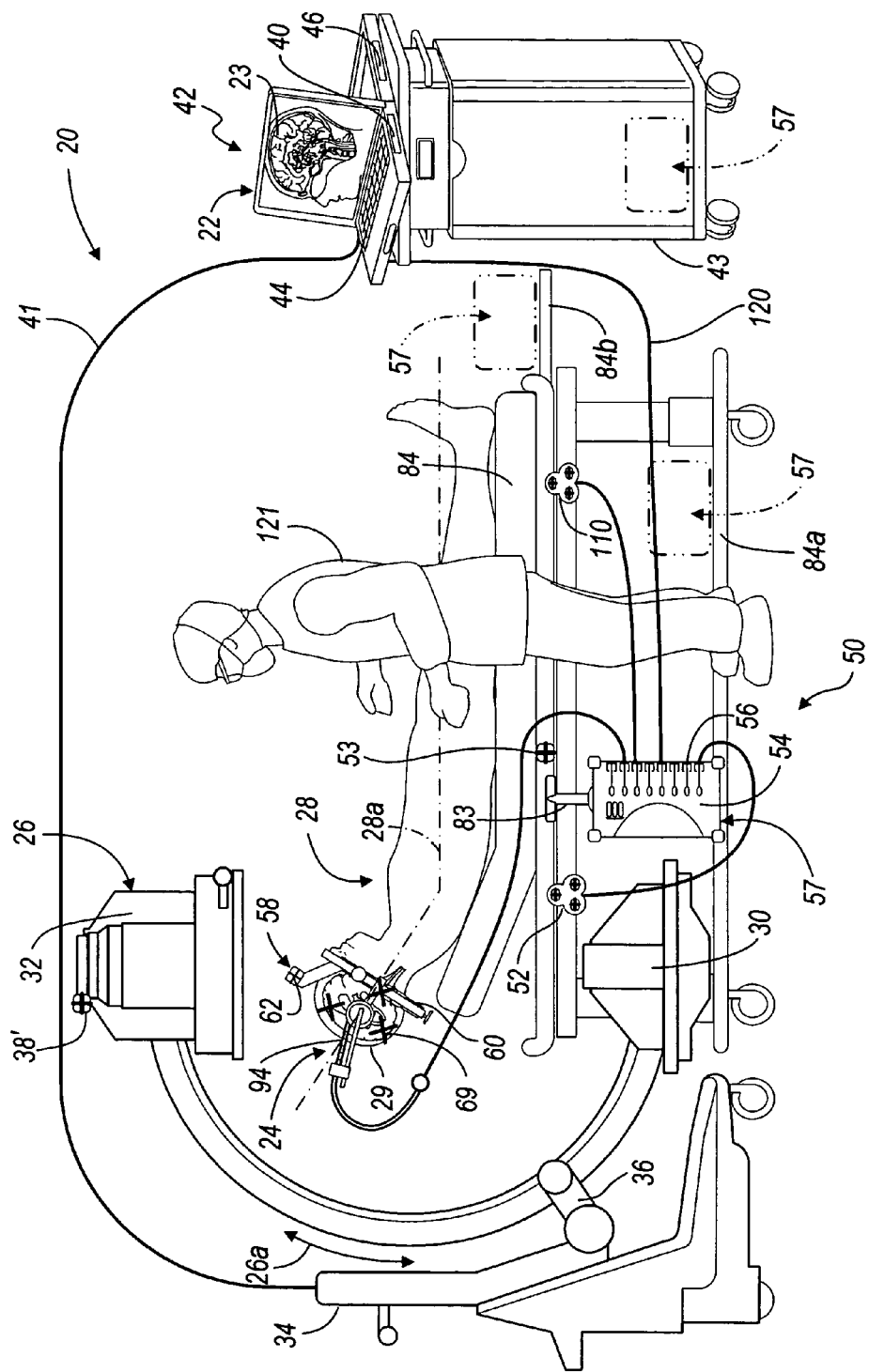
FIG. 1 is an environmental view of a navigation and tracking system according to various embodiments.

The following description is merely exemplary in nature and is not intended to limit the present disclosure, application, or uses. It should be understood that throughout the drawings, corresponding reference numerals indicate like or corresponding parts and features.

A guided procedure can be performed with a navigation system 20, in FIG. 1. The guided procedure can be any appropriate procedure, such as a neural procedure, spinal procedure, and orthopedic procedure. The navigation system 20 can include various components, as will be discussed further herein. The navigation system 20 can allow a user, such as a surgeon to view on a display 22 a relative position of an instrument 24 to a coordinate system. The coordinate system can be made relative to an image, such as in an image guided procedure, or can be registered to a patient only, such as in an imageless procedure.

Briefly, an imageless system can be provided which allows registration of an instrument to patient space, rather than image space. In an imageless system, image data of a patient need not be acquired at any time. Although image data can be acquired to confirm various locations of instruments or anatomical portions, such image data is not required. Further, the imageless system can be provided to allow for tracking a patient and an instrument relative to the patient.

In an exemplary imageless system, a determination of a position of an anatomical structure can be made relative to the instrument and the locations of each can be tracked. For example, a plane of an acetabulum can be determined by touching several points with a tracked instrument. The position of a femur can be determined in a like manner. The position of the relative portions, including the instrument and the anatomical portion, can be displayed on a display, with icons or graphics. The display, however, need not include image data acquired of the patient. One skilled in the art will understand that other data can be provided in an imageless system, however, like atlas data or morphed atlas data. Nevertheless, an imageless system is merely exemplary and various types of imageless or image based systems can be used, including the image base system discussed below.

It should further be noted that the navigation system 20 can be used to navigate or track instruments including: catheters, probes, needles, guidewires, instruments, implants, deep brain stimulators, electrical leads, etc. Moreover, the device can be used in any region of the body. The navigation system 20 and the various instruments 24 can be used in any appropriate procedure, such as one that is generally minimally invasive, arthroscopic, percutaneous, stereotactic, or an open procedure. Although an exemplary navigation system 20 can include an imaging device 26, one skilled in the art will understand that the discussion of the imaging device 26 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 26. The optional imaging device 26 or any appropriate imaging device can be used to acquire pre-, intra-, or post-operative or real-time image data of a patient 28. The illustrated imaging device 26 can be, for example, a fluoroscopic x-ray imaging device that may be configured as a C-arm 26 having an x-ray source 30 and an x-ray receiving section 32. Other imaging devices may be provided and reference herein to the C-arm 26 is not intended to limit the type of imaging device. An optional calibration and tracking target and optional radiation sensors can be provided, as understood by one skilled in the art. Image data may also be acquired using other imaging devices, such as those discussed herein. An example of a fluoroscopic C-arm x-ray device that may be used as the optional imaging device 26 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

An optional imaging device controller 34 can control the imaging device 26 to capture the x-ray images received at the receiving section 32 and store the images for later use. The controller 34 may also be separate from the C-arm 26 and/or control the rotation of the C-arm 26. For example, the C-arm 26 can move in the direction of arrow 26a or rotate about a longitudinal axis 28a of the patient 28, allowing anterior or lateral views of the patient 28 to be imaged. Each of these movements involves rotation about a mechanical axis 36 of the C-arm 26.

The operation of the C-arm 26 is understood by one skilled in the art. Briefly, x-rays can be emitted from the x-ray section 30 and received at the receiving section 32. The receiving section 32 can include a camera that can create the image data from the received x-rays. It will be understood that image data can be created or captured with any appropriate imaging device, such as a magnetic resonance imaging system, a positron emission tomography system, or any appropriate system. It will be further understood that various imaging systems can be calibrated according to various known techniques. Further, a C-arm tracking device 38' or any other imaging device can be provided to track a position of the receiving section 32 at any appropriate time by the navigation system 20.

The image data can then be forwarded from the C-arm controller 34 to a navigation computer and/or processor 40 via a communication system 41. The communication system 41 can be wireless, wired, a data transfer device (e.g. a CD-Rom or DVD-Rom), or any appropriate system. A work station 42 can include the navigation processor 40, the display 22, a user interface 44, and a memory 46. It will also be understood that the image data is not necessarily first retained in the controller 34, but may be directly transmitted to the workstation 42 or to a tracking system 50, as discussed herein. The workstation 42 can be any appropriate system such as a substantially portable computer system with an integrated display 22. The workstation 42 may include a laptop computer, such as a ruggedized laptop computer.

The work station 42 provides facilities for displaying the image data as an image on the displays 22, saving, digitally manipulating, or printing a hard copy image of the of the received image data. The user interface 44, which may be a keyboard, mouse, touch pen, touch screen or other suitable device, allows a physician or user to provide inputs to control the imaging device 26, via the C-arm controller 34, or adjust the display settings of the display 22. The work station 42 can also be used to control and receive data from a coil array controller (CAC)/navigation probe or device interface (NPI) 54/56.

While the optional imaging device 26 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 28. It should further be noted that the optional imaging device 26, as shown in FIG. 1, provides a virtual bi-plane image using a single-head C-arm fluoroscope as the optional imaging device 26 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 28, may be superimposed in more than one view on the display 22 allowing simulated bi-plane or even multi-plane views, including two and three-dimensional views.

With continuing reference to FIG. 1, the navigation system 20 can further include the tracking system 50 that includes a localizer 52, (e.g. which can also be referred to as a transmitter array, a tracking array, tracking coils, or coil array and can include a transmitter and/or receiver coil array), a coil array controller 54, a navigation interface 56, for an instrument tracking device and a dynamic reference frame 58. One skilled in the art will understand that the coil array 52 can transmit or receive and reference to a transmit coil array herein is merely exemplary and not limiting. The dynamic reference frame 58 can include a dynamic reference frame member or holder 60 and a removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including a localizer. Also the tracking device 62 can be wired to the other portions of the system or have a wireless communication therewith, as discussed herein.

The transmitter coil array 52 may also be supplemented or replaced with a second localizer 110. The second localizer 110 may be one such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. As is understood the localizer array can transmit signals that are received by the dynamic reference frame 58, and a tracking device 94. The dynamic reference frame 58 and the tracking device 94 can then transmit signals based upon the received signals from the array 52, 110.

It should further be noted that the entire tracking system 50 or parts of the tracking system 50 may be incorporated into the imaging device 26. For example, one of the localizers can be incorporated into the imaging device 26. Incorporating the tracking system 50 may provide an integrated imaging and tracking system. Any combination of these components may also be incorporated into the imaging system 26, which can include an appropriate imaging device.

The transmitter coil array 52 can be attached to the receiving section 32 of the C-arm 26. It should be noted, however, that the transmitter coil array 52 may also be positioned at any other location as well. For example, the transmitter coil array 52 may be positioned at the x-ray source 30, within or atop an operating room (OR) table 84 positioned below the patient 28, on siderails associated with the OR table 84, or positioned on the patient 28 in proximity to the region being navigated, such as on the patient's chest. The coil array 52 is used in an electromagnetic tracking system as the localizer therefore. The transmitter coil array 52 may also be positioned in the items being navigated, further discussed herein. The transmitter coil array 52 can include a plurality of coils that are each operable to generate distinct electromagnetic fields into the navigation region of the patient 28, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 52 is controlled or driven by the coil array controller 54. The coil array controller 54 drives each coil in the transmitter coil array 52 in a time division multiplex or a frequency division multiplex manner. In this regard, each coil may be driven separately at a distinct time or all of the coils may be driven simultaneously with each being driven by a different frequency, as discussed further herein. Upon driving the coils in the transmitter coil array 52 with the coil array controller 54, electromagnetic fields are generated within the patient 28 in the area where the medical procedure is being performed, which is again sometimes referred to as patient space. The electromagnetic fields generated in the patient space induce currents in the tracking devices 62, 94 positioned on or in the instruments 24. These induced signals from the instrument 24 are delivered to the navigation device interface 56 and can be forwarded to the coil array controller 54. The navigation probe interface 56 may provide all the necessary electrical isolation for the navigation system 20, as discussed herein. The navigation device interface 56 can also include amplifiers, filters and buffers to directly interface with the tracking devices 62, 94 in the instrument 24. Alternatively, the tracking devices 62, 94, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical cord to the navigation device interface 56.

When the navigation system 20 uses an EM based tracking system, various portions of the navigation system 20, such as tracking devices 62, 94, that can be associated with the (DRF) 58 and the instrument 24, are equipped with at least one, and generally multiple or more coils that are operable with the EM localizer arrays 52, 110. Alternatively, the tracking system may be a hybrid system that includes components from various tracking systems such as optical, acoustic, etc.

The EM tracking device 94 on the instrument 24 can be in a handle or inserter that interconnects with an attachment and may assist in placing an implant or in driving a portion. The instrument 24 can include a graspable or manipulable portion at a proximal end and the tracking sensor device that can be fixed near the manipulable portion of the instrument 24 or at a distal working end, as discussed herein. The tracking device 24 can include an electromagnetic sensor to sense the electromagnetic field generated by the transmitter coil array 52 that can induce a current in the tracking device 94.

The dynamic reference frame 58 of the tracking system 50 can also be coupled to the navigation device interface 56 to forward the information to the coil array controller 54. The dynamic reference frame 58, according to various embodiments, may include a small magnetic field detector as the trajectory device 62. The dynamic reference frame 58 may be fixed to the patient 28 adjacent to the region being navigated so that any movement of the patient 28 is detected as relative motion between the transmitter coil array 52 and the dynamic reference frame 58. The dynamic reference frame 58 can be interconnected with the patient in any appropriate manner, including those discussed herein. Any relative motion is forwarded to the coil array controller 54, which updates registration correlation and maintains accurate navigation, further discussed herein. If the dynamic reference frame 58 is electromagnetic it can be configured as a pair or trio of orthogonally oriented coils, each having the same center or may be configured in any other non-coaxial or co-axial coil configurations.

The dynamic reference frame 58 may be affixed externally to the patient 28, adjacent to the region of navigation, such as on the patient's cranium, etc., as shown in FIG. 1. The dynamic reference frame 58 can be affixed to the patient's skin, by way of a selected adhesive patch and/or a tensioning system. The dynamic reference frame 58 may also be removably attachable to a fiducial marker 69. The fiducial markers can be anatomical landmarks or members attached or positioned on the patient's 28 body. The dynamic reference frame 58 can also be connected to a bone portion of the anatomy. The bone portion can be adjacent, the area of the procedure, the bone of the procedure, or any appropriate bone portion.

Briefly, the navigation system 20 operates as follows. The navigation system 20 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the C-arm controller 34 identify the corresponding point on the pre-acquired image or atlas model relative to the tracked instrument 24 and display the position on display 22 and relative to the image data 23. Although each of the systems can be incorporated into a single system or executed by a single processor. This identification is known as navigation or localization. An icon representing the localized point or instruments is shown on the display 22 within several two-dimensional image planes, as well as on three and four dimensional images and models.

To register the patient 28, a physician or user 121 may use point registration by selecting and storing particular points from the pre-acquired images and then touching the corresponding points on the patient's anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 69, such as anatomical or artificial landmarks. Again, the fiducial markers 69 are identifiable on the images and identifiable and accessible on the patient 28. The fiducial markers 69 can be artificial landmarks that are positioned on the patient 28 or anatomical landmarks that can be easily identified in the image data. The artificial fiducial markers 69, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 69 rather than being the fiducial marker 69.

The system 20 may also perform registration using anatomic surface information or path information as is known in the art (and may be referred to as auto-registration). The system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 20 continuously can track the position of the patient 28 during registration and navigation with the dynamic reference frame 58. This is because the patient 28, dynamic reference frame 58, and transmitter coil array 52 may all move during the procedure, even when this movement is not desired. Alternatively the patient 28 may be held immobile once the registration has occurred, such as with a head frame. Therefore, if the navigation system 20 did not track the position of the patient 28 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 28, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 28, and can be used to register the patient to the image data, as discussed above. For example, when a procedure is being performed relative to a cranium 29, the dynamic reference frame 58 can be interconnected with the cranium 29. The dynamic reference frame 58 can be interconnected with the cranium 29 in any appropriate manner, such as those discussed herein according to various embodiments.

Navigation can be assisted with registration and the navigation system 20 can detect both the position of the patient's anatomy and the position of the device 58 or attachment member (e.g. tracking sensor 84) attached to the instrument 24. Knowing the location of these two items allows the navigation system 20 to compute and display the position of the instrument 24 or any portion thereof in relation to the patient 28. The tracking system 50 is employed to track the instrument 24 and the anatomy 28 simultaneously.

The tracking system 50, if it is using an electromagnetic tracking assembly can work by positioning the transmitter coil array 52 adjacent to the patient space to generate a magnetic field, which can be a low energy, generally referred to as a navigation field. Because every point in the navigation field or patient space is associated with a unique field strength, the electromagnetic tracking system 50 can determine the position of the instrument 24 by measuring the field strength at the tracking device 94 location. The dynamic reference frame 58 is fixed to the patient 28 to identify the location of the patient 28 in the navigation field. The electromagnetic tracking system 50 continuously recomputes the relative position of the dynamic reference frame 58 and the instrument 24 during localization and relates this spatial information to patient registration data to enable image guidance of the instrument 24 within and/or relative to the patient 28.

To obtain a maximum accuracy it can be selected to fix the dynamic reference frame 58 in each of at least 6 degrees of freedom. Thus, the dynamic reference frame 58 or any of the tracking device 62 can be fixed relative to axial motion X, translational motion Y, rotational motion Z, yaw, pitch, and roll relative to the portion of the patient 28 to which it is attached. Any appropriate coordinate system can be used to describe the various degrees of freedom. Fixing the dynamic reference frame relative to the patient 28 in this manner can assist in maintaining maximum accuracy of the navigation system 20.

The instrument 24 can be any appropriate instrument (e.g., a catheter, a probe, a guide, etc.) and can be used for various mechanisms and methods, such as delivering a material to a selected portion of the patient 28, such as within the cranium 29. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 28 in any appropriate manner, such as within the cranium 29. The instrument 24 may also include a brain probe to perform deep brain stimulation.

Figure 2:
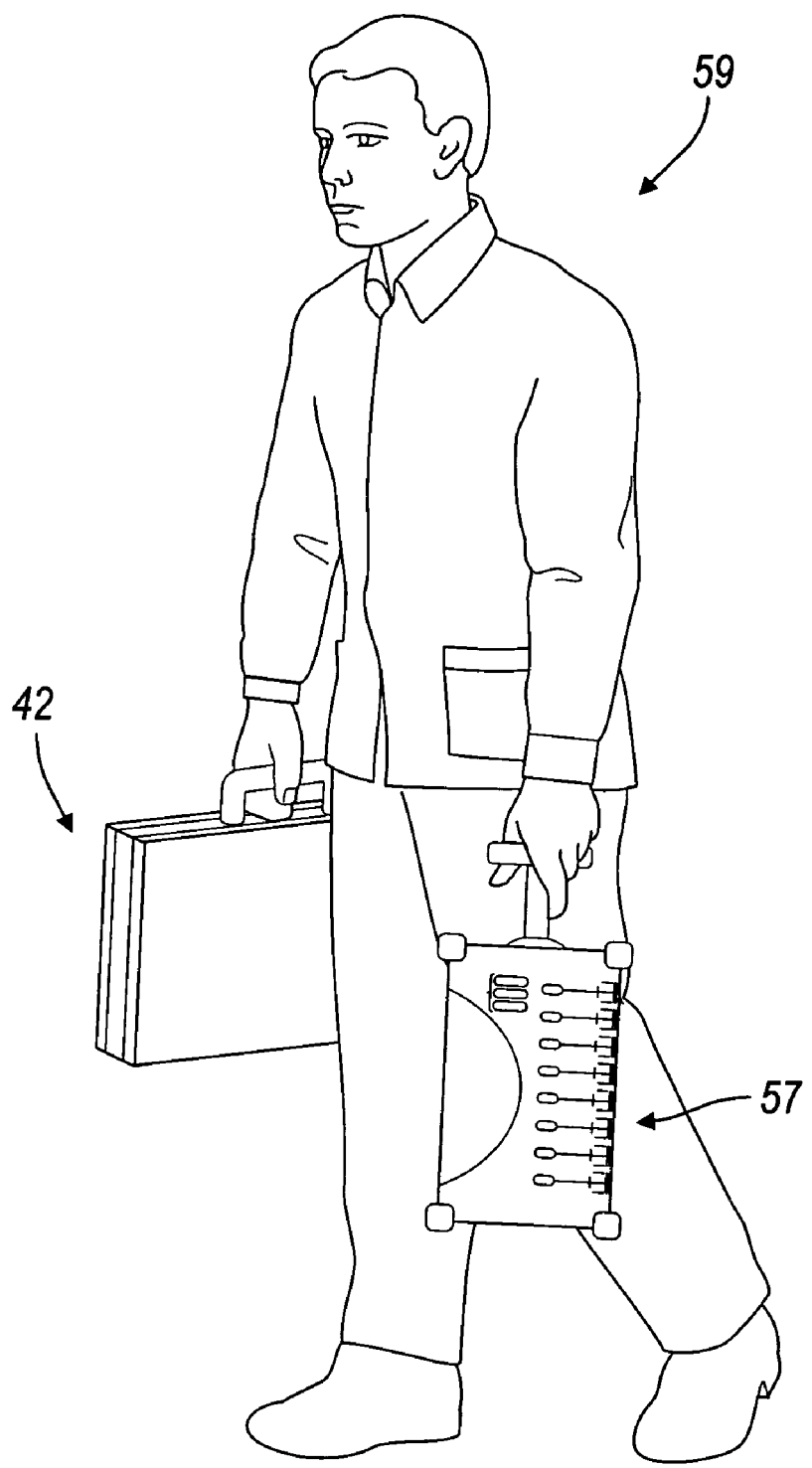
FIG. 2 illustrates an individual maneuvering components of a navigation system according to various embodiments.

With reference to FIG. 2, the tracking system 50 according to various embodiments, can include the CAC 54 and the navigation probe interfaces (NPI) 56 in a single substantially small CAC/NPI container 57. It will be understood that the CAC/NPI container 57 can be any appropriate size, but can generally include a volume of about 32 cc to about 9850 cc (about 2 in.$^3$ to about 600 in.$^3$) and having a mass or weight on Earth of about 2 kg to about 10 kg (5 pounds to about 22 pounds). It will be understood, however, that the CAC/NPI can be about 1 m$^3$, or any appropriate size. The module 57 can generally be provided in a container or size that is substantially portable. The CAC/NPI container 57 can allow for ease of use and portability from area to area by a single user 59. The coil tracking array 52 can also be provided in a substantially small package, which can also have a volume of about 4916 cc to about 0.42 m$^3$ (about 300 in.$^3$ to about 15 ft.$^3$). It will be understood that the dimensions of the coil array can include the volume in any appropriate dimensions such about 10 in. by 16 in. by 3 in., but also can include appropriate dimensions of more than two or three feet in each dimension and still include an appropriate portability.

As illustrated in FIG. 2, the single user 59 can easily transport the CAC/NPI 57 container and the work station 42 from area to area. The CAC/NPI container 57 and the container of the workstation can both be made of rugged and/or durable material. For example, metal or high impact plastics can be used as a part of the case. In addition, shock absorption, moisture absorption, and protection devices can be included in the CAC/NPI container 57 and the workstation 42. The ruggedized construction can be provided to minimize breakage and increase stability of the navigation system 20, especially over a period of time. Also, sealed cases can be provided for various portions. The various components can be provided in a size and mass that are easy for the user 59 to move without substantial assistance of further individuals. The coil array 52, or the multiple arrays 110, 112, 114 can be carried in a container including the workstation 42 or separate therefrom. As discussed herein the work station 42 can be included in a rugged container than can include storage space or other hardware, such as the array 52.

In addition, with reference to FIG. 1, the CAC/NPI container 57 can be positioned in an operating room in any appropriate location. For example, a handle or hanging portion 83 can be used to hang the CAC/NPI container 57 from the operating table or operating bed 84. Further, the CAC/NPI container 57 can be positioned on a lower level or shelf 84a of the operating table 84. The lower level 84a can allow a position for the CAC/NPI container 57 to be positioned out of the way of the surgeon 121 or other operating room staff. In addition, the CAC/NPI container 57 can be positioned on a foot end or on an end 84b of the operating table 84. Often operating room tables are designed with open space on various portions of the operating room table 84 and the CAC/NPI container 57 can be positioned thereon. The open space is generally of fairly similar or specific dimensions, such as about 1.5 feet by about six inches, and the CAC/NPI container 57 can be dimensioned to easily and conveniently fit in this area. Alternatively, the CAC/NPI container 57 can be positioned on the cart 43 that can be used in the operating room or moved from operating room to operating room. The cart 43 can also provide an area for the work station 42 to be positioned for use by the surgeon 121 or appropriate operating room staff. Therefore, the CAC/NPI container 57 can be positioned in any appropriate location as can the work station 42. Further, the size and mass of the CAC/NPI container and the work station 42 can allow them to be easily moved from location to location for various or multiple procedures.

Figure 3:
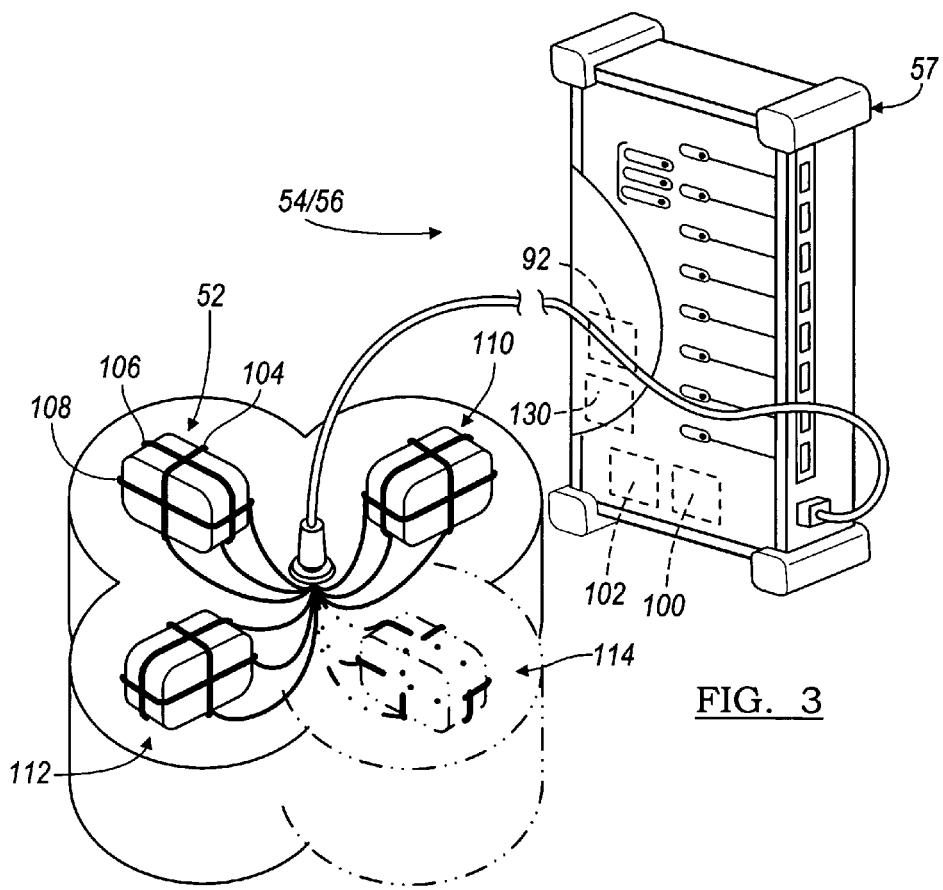
FIG. 3 is a detailed view of a tracking array according to various embodiments.

Turning reference to FIG. 3, the CAC/NPI controller can include various portions, including those discussed further herein in detail, to control and power the array 52. The array 52 can be provided as a single or multiple coils that can be positioned relative to a single axis or origin as discussed further herein. Further, a plurality of individual coil arrays can be provided as the coil array 52, also as discussed further herein. The various portions that can be controlled by the controller and the amplifiers, further discussed herein, are generally illustrated schematically in FIG. 3.

It will be understood that in an electromagnetic system, a plurality of coils, such as a first coil 104, a second coil 106, and a third coil 108 can be provided as substantially orthogonal angles to one another and can be powered to produce an electromagnetic field at least in part depending upon the orientation of the selected coil 104, 106, 108, relative to the other coils. It can be selected to provide more than a single set of coils or a single array within the tracking system 50. Therefore, the transmitter coil array 52 can also include a second set of coils or array 110 that can also include three orthogonally placed coils, a third set of coils or array 112 that can include three orthogonally placed coils, and a fourth set of coils or array 114 that can also include three orthogonally placed coils.

Each of the sets of coils can form a coil array to be controlled by the CAC 54, as discussed further herein. Generally, each array will have three separate coils of wire, exemplary illustrated in FIG. 3. It will be understood, however, that each array may have more or fewer than three coils.

It will be understood that any appropriate number of coils or arrays can be provided and three or four arrays is merely exemplary and any appropriate number can be provided. Nevertheless, the CAC 54 can power or control the coils of the transmitter array 52 using switches 100 and a coil amp 102. Also, the array 52 can be configured as a receiving array, as discussed above, for use in the navigation system 20.

It will be understood, also, that the various arrays 52, 110, 112 and 114, can be provided and displaced or positioned a distance from one another so that they are not contained within the single transmitter array. For example, a first array 52 of the coils can be provided beneath the patient 28 on a portion of the patient bed 84, while a second array 110 can be provided to be held by a user 121 while other arrays can be provided at various locations within the operating theatre. Therefore, providing each of the coil arrays in a single box or container is merely exemplary for clarity of the current discussion. In other words, each of the coil arrays 52, 110, 112, and 114 can be positioned relative to the patient 28 in any appropriate manner. Nevertheless, the coil amplifier 102 can be provided as a single amplifier for each of the individual coils in each of the coil arrays. It will be understood that the discussion regarding each of the individual coils 104, 106, 108 of the array 52 can be applied to individual coils in each of the other arrays 110, 112, 114, yet not be repeated for purposes of the current teachings.

The amp 102, therefore, can provide a single amp or an amp section for each of the single coils 104, 106, 108. The amplifier 102 can also be provided to provide amps to each of the other array sets 110, 112, 114. The switch 100 can be used to switch between the various coil arrays 110, 112, 114 or amongst the individual coils, such as individual coils 104, 106, 108. Therefore, the arrays can be switched for use during an operating procedure so that different information can be obtained from each of the different arrays or a confirmation of information can be obtained.

For example, it may be provided to include a plurality of the coil arrays within the operating theatre to confirm the information being obtained from each one of the single arrays. If the array 110 is being used to track the instruments 24, the array 112 can be positioned at the location different from the location of the array 110 so that the position of the instruments 24 relative to the patient 28 can be confirmed with the second array. Also, multiple arrays 52, 110, 112, 114 can be provided to obtain high degree of freedom information about the tracking devices 62, 94.

The coil switches 100 can be substantially digital switches to allow for substantially fast switching amongst the different coil arrays. Digital switches can include MOSFET digital switches. Further, the digital switches can be used to switch quickly between each of the various coil arrays 52, 110, 112, 114 to allow for substantially simultaneous tracking of multiple instruments with different arrays. Therefore, not only can the navigation or tracking of a single or multiple tracking devices 94 be done substantially simultaneously due to the switching of the various coils, but different instruments can be tracked with different arrays to allow for reduction of interference between the different coil of the tracking system 50.

Figure 4:
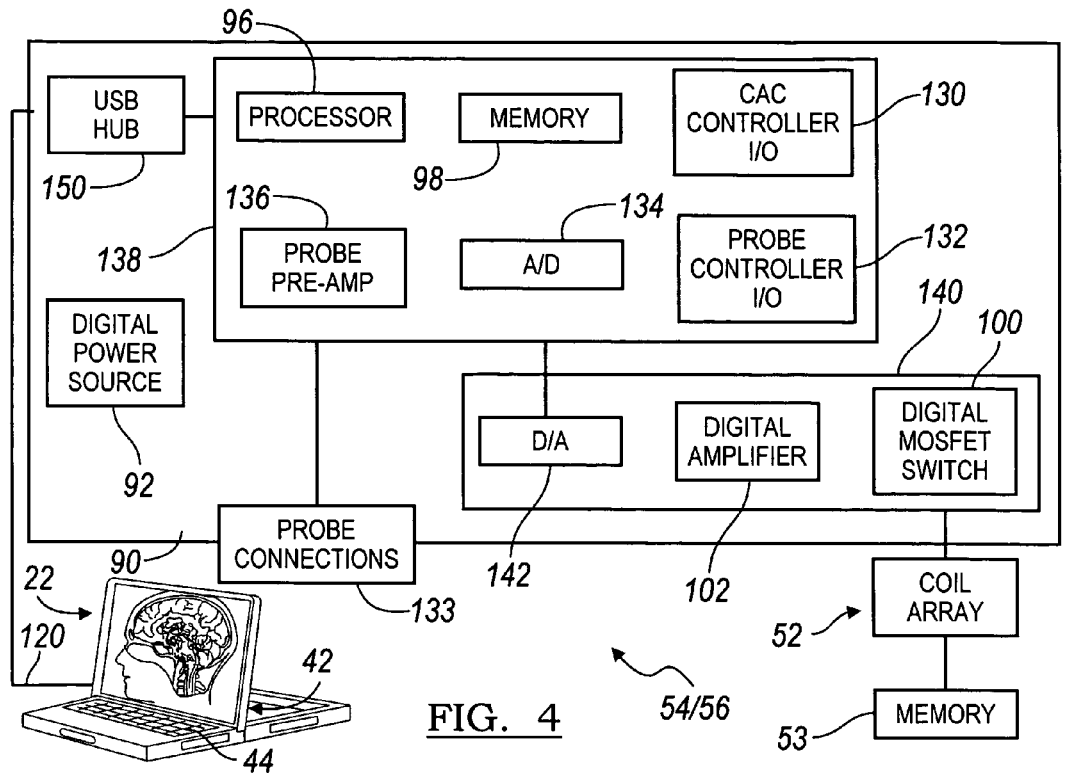
FIG. 4 is a general block diagram of an electronics portion of a tracking system.

With reference to FIG. 4, a block diagram of an electronics portion of the CAC 54 and NPI 56 is illustrated which can be housed in the single CAC/NPI container 57 according to various embodiments. The CAC 54 and the NPI 56 operate with the workstation to navigate the instrument 24, as discussed herein. A processor 96 can be provided with a memory 98 to process various data and to execute selected instructions. Further, a CAC controller I/O portion 130 can be provided to control and provide various inputs and outputs regarding the array 52. For example, the CAC controller portion 130 can include wave form generators, data conduits, various sensors, and the like. The CAC controller 130 can include various portions to allow for communication between the CAC controller 130 and a probe controller 132, as discussed further herein. Further, the CAC controller 130 can communicate with the processor 96 and the memory 98 to allow for controlling of the coil array 52.

The probe controller 132 can be interconnected with the CAC controller 130 and therefore with the processor 96 to communicate with a probe connection 133 of the NPI 56. The probe controller 132 can also include various portions such as a communication line, input and output connections, and the like. Further, the probe controller 132 can be interconnected with an analog-to-digital converter 134. The A/D converter 134 can be interconnected with a probe pre-amp 136 that is connected to the probe connections 134. The probe pre-amp 136 can amplify a signal to or from the instrument 24 that is interconnected with the probe connections 134 for communication through the analog digital converter 134, the probe controller 132, and to the processor 96. The probe pre-amp 136 can amplify a signal to or from the tracking device 94 interconnected with the instrument 24 to determine the position of the tracking device 94 in the navigation field produced by the coil array 52. Therefore the signal received from the tracking device 94 can be processed by the processor 96 to determine a position and/or orientation of the tracking device 94 relative to the coil array 52.

It will be understood by one skilled in the art that the analog to digital converter 134, the probe pre-amp 136, and the probe connections 133 can be generally understood connections. For example, the probe connections 133 can include universal serial bus connections (USB) for communication between the tracking device 94 and the processor 96. Also the probe connections 133 can be interconnected with any number of tracking devices such as the tracking device 62. It will be understood that wireless communications can also be used rather than wired connection interfaces.

The NPI 56 can include various portions including those discussed above. The NPI can include the probe controller I/O, the A/D converter 134, the probe connections 133, and the probe pre-amp. Though other portions may be included, these portions generally form the NPI 56.

As discussed above, the digital power source 92 can be provided to supply a power to the CAC 54 and the NPI 56 in a substantially isolated manner. The digital power source 92 can provide the isolation from the patient 28 in various manners, as understood by one skilled in the art. However, the use of the digital power supply can eliminate or reduce the need for large components to isolate the patient 28 from the electrical supply in the CAC 54.

The various components, including the processor 96, the memory 98, the CAC controller 130, the probe controller 132, the A/D 134, and the probe pre-amp 136 can be included or provided as a processing system 138 of the CAC 54 and the NPI 56. A coil array driving portion 140 can be provided that is interconnected or in communication with the processing portion 138. The coil array driving portion 140 can be included with the CAC controller I/O 130 as the CAC 54.

The coil array driving portion 140 can include a digital to analog (D/A) converter 142. The D/A converter 142 can form a signal for the digital amplifier 102 which can drive or provide a current through the digital MOSFET switch 100. The current can be switched by the MOSFET switch 100 to the various coils in the array 52.

The drive signal can be provided by the D/A converter 142 that is provided substantially on board the coil array controller portion 140 or near the amplifier 102. Providing the D/A 142 substantially on a board with the digital amplifier 102 can help reduce or substantially eliminate noise pick up by the digital amplifier 102. Further, the digital amplifier 102 can be provided to provide an output current through the digital MOSFET switch 100 to the coil array 52 in a selected manner. Generally, the digital amplifier 102 can substantially eliminate the possibility of a magnetic field producing a voltage in an amplifier before the switch 100 that would disturb the current being amplified by the digital amplifier 102 from the D/A 142.

The digital MOSFET switch 100 can be provided to allow switching from the digital amplifier 102 to the coil array 52. As discussed above, the coil array 52 can be provided as a plurality of coil arrays that can include a plurality of individual coils. According to various embodiments, a selected number of the digital MOSFET switches 100, such as 3, 4, or any appropriate number can be provided for the digital amplifier 102. Also, a plurality of the digital amplifiers 102 can also be provided.

According to various embodiments, the coil array 52 can include a plurality of coils that would each include or be interconnected with one of the plurality of digital amplifiers. If a plurality of coil arrays were provided, a digital switch could be provided between each of the digital amplifiers and a selected one of the individual coils. Therefore, according to various exemplary embodiments, further illustrated in FIG. 5, a plurality of the digital amplifiers can include three digital amplifiers 102a, 102b, 102c, to amplify a signal to drive each of one of three coils provided in the coil array 52. As discussed above, three coils can be positioned in each of a coil array 52, 110, 112, 114 in a selected orientation, such as substantially orthogonal to one another around a single center point. The digital MOSFET switch can be provided as three sets of four digital MOSFET switches 100a, 100b, 100c that are interconnected with each of the respective digital amplifiers 102a, 102b, 102c. The sets of digital MOSFET switches 100a, 100b, 100c can be provided to quickly switch between each of the coil arrays 52, 110, 112, 114 to selectively drive each of the coils in the various coil arrays 52, 110, 112, 114. The multiple coil arrays 52, 110, 112, 114 can be provided for various reasons such as providing multiple degrees of freedom for determination of the position of the tracking device 62, 94, to provide redundancy between the various coil arrays 52, 110, 112, 114, or various other reasons.

Returning briefly to FIG. 4, the CAC/NPI container 57 can include a USB hub connection 150 to interconnect with the communication wire 120 to the workstation 42 with the CAC 54 and NPI 56. As discussed above the work station 42 can include an imaging controller processor 40. Various processing steps can be selected and either the processor 96 or the processor 40 can perform the steps. It may be selected to allow the processor 96 in CAC/NPI 54/56 to provide coordinates of the tracking devices 62, 94, such as X, Y and Z components, and transmit them over the communication line 120 to the work station 42. The processor 40 in the work station 42 can then be provided to process the image data, determine a location of the X, Y, and Z component relative to the image data, and display the processor determined location of the X, Y, and Z component on the display 22.

Figure 7:
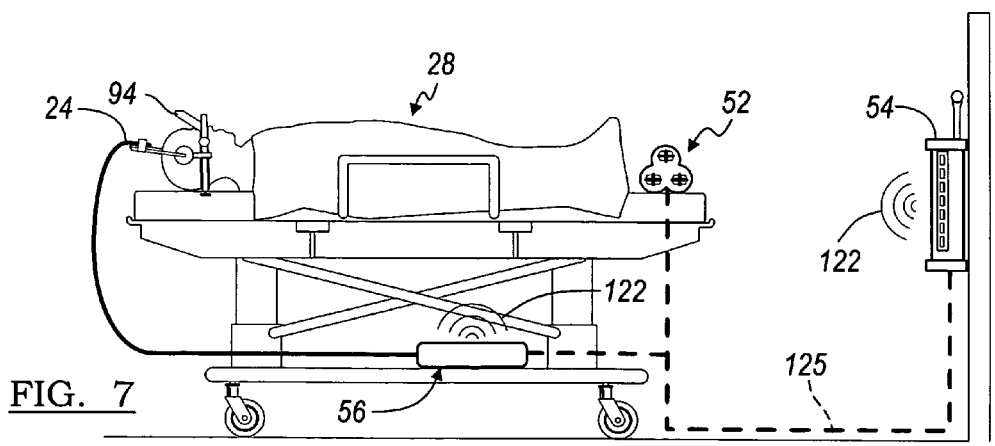
FIG. 7 is a perspective view of a tracking system.

The tracking system 50, as illustrated above, need not be provided in a single unit. For example, as illustrated in FIG. 7, various components of the tracking system 50 can be provided as substantially individual components. For example, the probe interface component 56 can be provided separate from the CAC 54. This system can be used because the probe interface component 56 can be substantially low powered or low current. For example, only a small amount of power may be required to amplify a signal from the tracking device 94, power the wireless transmission 122, etc. Also, the NPI 56 can substantially include only interface components to allow for transfer of information from the tracking device 94 to the CAC 54 for processing, as discussed above. Therefore, the NPI 56 may not require external or forced air cooling, therefore the NPI 56 could be substantially sealed and positioned near the patient 28 without worry of materials infiltrating the probe interface component 56. The tracking array 52 can also be provided substantially near the patient due to the sealed nature of the tracking array 52.

The NPI 56 and the tracking array 52 can be connected via a communications system with the CAC 54. The communications system can include a wire system including a communication wire 125 which can be substantially similar to the wire interface 120 illustrated in FIG. 1. The wire interface 125 between the CAC 54 and the NPI 56 can allow for communication of information, such as the interface information including the tracked location of the tracking device 94. It will also be understood that various other communication systems can be used such as a wireless communications system 122. The wireless communications system can include any appropriate wireless communications systems such as generally known Bluetooth® systems, wireless LAN systems, and the like. Further, signal robustness can be provided due to frequency hopping, spread spectrum transmission, and other signal robustness techniques. The signal robustness techniques of the wireless communication system 122 can be provided for various purposes. For example, electronic components provided in the operating theater may interfere with certain systems; therefore it can be selected to provide the robustness of the wireless communication system 122.

It will also be understood that the tracking array 52 can be wired with the wired communication system 122 or with a separate wire communication system, if selected. Nevertheless, a wireless transmission system can be provided to transfer certain information between the tracking array 52 and the CAC 54. Although various components may be positioned near the tracking array, such as the amplifier 102, various other components can be positioned a distance in the CAC 54. Also, the communication system 120 can be provided to communicate with the workstation 42 which can also include the wireless communication system 122.

It will be understood that the CAC 54 can be provided with various components, such as the processor 96, the switch 100, the power supply 92, and other various components. These components may be selected to be cooled with forced air cooling which may require vents being formed in the exterior of the CAC 54. Therefore, the position of the CAC 54 can be selected a distance from the patient 28 to substantially eliminate or reduce the possibility of material infiltrating the CAC 54. Nevertheless, the communications system, including the wired communication system 125 or the wireless communication system 122, can be provided so that various components such as the probe interface 56 and the tracking array 52 can be positioned near the patient 28. Further, the wireless system 122 can be selected for various purposes, such as eliminating additional hardware being positioned or draped across the patient 28 or near the patient 28 which can allow for a more efficient surgical procedure.

Further, it will be understood that the various coil arrays 52, 110, 112, and 114 can include various information that is specific to each of the particular coil arrays 110, 112, and 114. For example, each of the coil arrays 110, 112, and 114 can be provided with calibration information, the type of the array, or the like. The various coil arrays 52, 110, 112, 114 can include a memory system 53 that can include the various calibration and particular information about the particular coil array 52. The memory 53 can be integral with the coil array or be provided on various flash or static memory devices, such as ROM cards, flash memory devices, and the like.

The various techniques can also be provided to substantially ensure a robust and properly operating system. For example, the memory 98 can include various diagnostic components that can be run at start up of the CAC/NPI 54/56. The diagnostics and the memory 98 can be processed by the processor 96 such that during each start up the CAC/NPI 54/56 would be diagnosed for certain issues that may occur. If any issues are detected with the diagnostics, the communication line 120 could be used to communicate any errors to the display 22 on the work station 42 for determination or analysis by a user. Further, the diagnostics could be run in a substantially automated system during production of the CAC/NPI 54/56 during production thereof. This can eliminate or reduce the necessity of manual diagnostics over the CAC/NPI during use of the system.

With reference to FIG. 7, portions of the tracking system 50 and the workstation 42 can be positioned in a single container 141. The single container 141 can include any of the multiple portions discussed above. For example, the navigation container 141 can include the NPI 56, the CAC controller 54, the display 22, a processor or multiple processors 96 and a storage area 70. The navigation container 141 can be provided for use and transport by a single user and for ease of operation by a single user. The navigation container 141 can include each of the components discussed above, including the work station 42 and the CAC 54, and the NPI 56. Including each of the components in the single navigation container 141 can provide for ease of use, as discussed herein.

The hardware storage area 70 of the navigation container 141 can be used to store various portions, such as interface cords 72 that can interconnect the instruments 24 with the navigation container 141. The communication cord 72 can be provided in any appropriate manner, such as including a USB port or connector 74. It will be understood that the USB connector 74 is merely exemplary and any appropriate interconnection can be provided for the instrument connections with the probe interfaces 56. It will be further understood that various wireless receiving communications systems 76 can be provided. For example, the wireless systems 76 can include a first portion 78 that can interconnect with the NPI 56 and a second portion 80 that can interconnect with the instrument 24. It will be understood that various other systems can be provided, and this is merely exemplary and will be discussed further herein. The hardware storage area 70 can also be provided to store the coil array 52. Therefore, the tracking system 50 can be carried in a substantially single container from place to place by a user.

The navigation container 141 can also include a carrying handle and a mounting handle 82. The carrying handle 82 can be provided at any appropriate location on the navigation container 141 to allow for ease of transport. The handle 82 or any other appropriate connection portion can be used to interconnect the navigation container 141 with a selected portion in the operating theatre. For example, the handle 82 can be interconnected with a patient bed 84, such as by hanging the tracking system 50 from the patient bed 84. The coil array 52 can also be provided relative to the patient 28, as illustrated in FIG. 1.

The navigation container 141 can also include an electronic storage or containment area 90. The electronics containment area 90 can be provided to perform various functions, such as containing the electronic storage from the tracking system from environmental concerns. Therefore, the electronic components can remain substantially sterilized and do not need cleaning from one use to another.

Within the electronics containment area 90, various components can be provided. Briefly, a digital power supply 92 can be provided to be interconnected with a selected power supply, such as an alternating current supply. The digital power supply 92 can provide various features, such as isolation of the patient 28 from a shock or surge from the tracking system 50. The digital power supply can be any appropriate digital power supply, such as the digital power supply JPS130PS24-M, supplied by XP Power. The digital power supply can be interposed between the incoming power supply to the tracking system 50 and the supply power to the instruments interconnected with the NPI 56. The digital switching of the power supply 92 can substantially eliminate the possibility of a shock being transmitted through the tracking system 50 to a tracking device 94 interconnected with the instrument 24. Because of the digital power supply 92, the tracking device 94 can be powered to be used with the tracking system 50 without requiring a separate isolation system between the tracking system 50 and the tracking device 94. As discussed further herein, one or more of the tracking devices can be interconnected with the instruments 24 for obtaining various data regarding the instrument 24. Further, it will be understood that a plurality of instruments may be used with the tracking system 50 at a selected time, also discussed further herein, and the illustration of the single instruments 24 is merely exemplary for clarity of the current teachings.

The electronics component area 90 can also include a processor 96 and a memory or storage system 98. The processor 96 can be any appropriate processor, such as the processors generally provided by various companies, including the companies of Intel®, Motorola®, AMD®, or the like. The processor 96 can be used to process various information including the tracked position of the instrument 24 and also controlling the coil array 52. The processor 96 can be provided with an appropriate amount of processing power to perform various functions, or to perform multiple functions substantially simultaneously. For example, the processor 96 can be interconnected with the ports 56 to receive information regarding the tracking devices 94. The processor 96 can also be provided to simultaneously process the image data.

Figure 5:
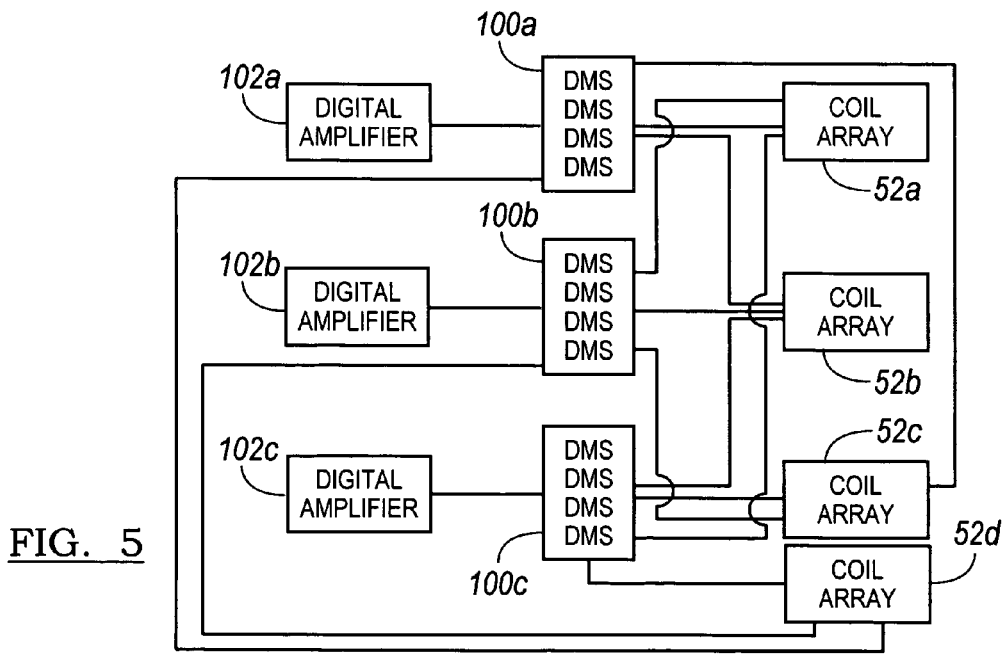
FIG. 5 is a detail block diagram of an amplifier and switch system to drive a coil array according to various embodiments.
Figure 6:
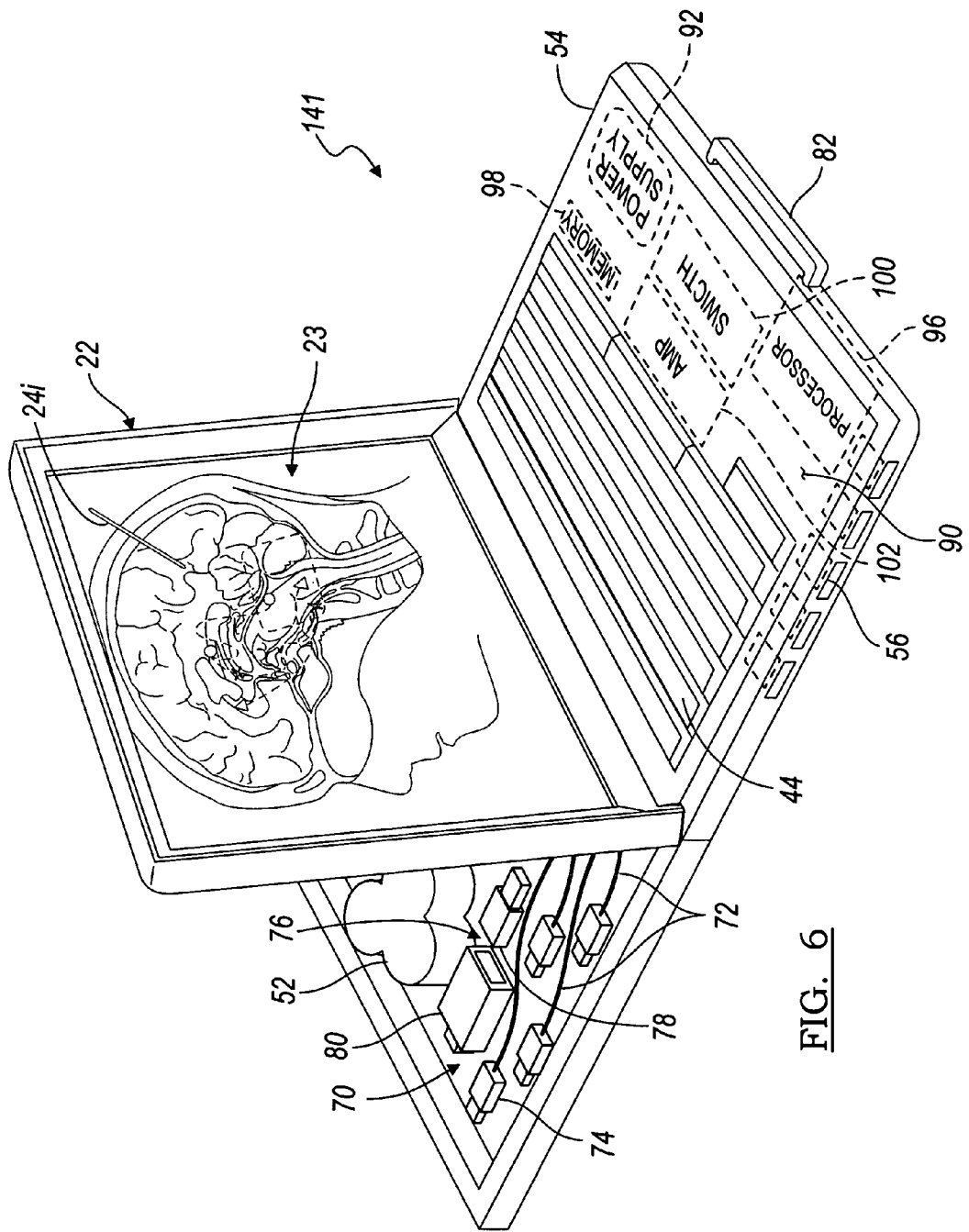
FIG. 6 is an environmental view of a tracking system according to various embodiments.

Further, the electronic components area 90 can include the coil switch 100 and the coil amp 102. Although the coil switch 100 and the coil amp 102 are generally provided to allow for switching among the various coils in the coil array 52, the processor 96 can also be provided to control many different coil switches 100a, 100b, 100c (FIG. 5). Therefore, the processor 96 can be provided for both controlling the coil array 52 and navigating the instruments 24 based upon the tracking device 94. Further, the memory 98 can be provided to store various information, such as calibration for instruments, previous tracked positions of the instruments 24, calibrations for the coil switch 100 and the coil amp 102 and any other appropriate information. The memory 98 can also be used to store the image data to be processed by the processor 96 and displayed on the display 22. The memory 98 can be any appropriate memory, such as a solid state memory, a hard disk memory, or other appropriate memory types.

The coil amp 102 and the coil switch 100 can be provided to amplify power to the coil array 52 and to switch among the various coils in the coil array 52. For example, the coil array 52 can include a plurality of sets of coils that can, for example, transmit electromagnetic fields into the operating theatre, such as around the patient 28 or near the area where the instrument 24 is being used. As discussed above, appropriate electronic components can be positioned and used in the navigation container 141.

As discussed above, the navigation container 141 can also include the coil amp 102 that can be used to amplify power to any of the number of coils provided in the coil array 52, as exemplary illustrated in FIG. 3 with the CAC/NPI container 57. According to various embodiments the navigation container can include the components to power and control the array 52.

The navigation container 141 can also include the display 22 integral with a portion thereof. The display 22 can be used to display the various images, such as image data 23 of the patient 28. The display 22 can be any appropriate display such as an LCD display commonly used on laptop computers. The image on the display 22 can also display a representative location of the instrument 24 relative to the image data 23. The image data 23 can include any appropriate image data, including that described above from the C-arm 26, an MRI, a CT scan, or the like. Nevertheless, the image data 23 can be registered, also as described above, to allow for an appropriate representation of the instrument 24 relative to the image data 23. The representation could include an icon 24i of the instrument illustrating a position of the instrument 24 relative to the image data 23. The processor 96 can be used to process both the navigation of the instrument 24, allowing for an indication with the icon 24i of the instrument on the image data 23, and for the control of the array 52. Therefore the processor 96 can be provided in any appropriate power to allow for processing of multiple systems, such as the navigation system, the imaging system, or any other appropriate system. Again, this can allow for minimizing or reducing the size of various components by providing for multiple processes to occur in a single processor 96. It will also be understood that the memory system 98 can include various information such as the image data, the instructions to be executed by the processor 96 to perform the navigation and the processing of the image data, and other appropriate information.

As discussed above, various systems, according to various embodiments have been illustrated and described. It will be understood, however, that the various systems can be combined or separated for various purposes. Nevertheless, the navigation system 20, according to various embodiments, can be provided as a multiple or single component or container system. For example, as illustrated in FIGS. 1 and 2, two components can be provided. The two components can include a first component which can be the work station 42 and a second component which can be the CAC/NPI container 57 which includes the CAC 54 and the NPI 56. The two containers, however, can be easily transported by the single user 59 from procedure to procedure or from a manufacturer to a user. Alternatively, or in addition thereto, various components can be separated for various reasons, such as space saving, instructional integrity, and the like. As illustrated in FIG. 7, the NPI 56 can be separated from the CAC 54 for various purposes, such as positioning a substantially sealed container in an area that may be exposed to liquids while removing a container that may not be sealed away from the fluids. Also, according to various embodiments, a single container such as a navigational container 141 can include all relevant components and a storage area for the hardware of the system. Therefore, the image processor and/or workstation 42, the CAC 54, the NPI 56, a storage area for hardware 70, and various other portions can be included in or as part of the navigation container 141.

Also, the provision of a substantially smaller portable size container can allow for ease of manipulation and transport from location to location. In addition, the small size can reduce heat production that can assist in eliminating or substantially reducing interference with various components, such as in the array 52 or of the amplifier 102.

What is claimed is:

1. A navigation system for use in an operating theatre to navigate a procedure relative to a patient, comprising:
   a coil array having at least three separate coils of conductive material operating with a selected transmission system that is operable to at least one of transmit a first field, receive a second field, or combinations thereof that is changed by at least one of a time differential, a time duplex, a frequency duplex, or combinations thereof;
   an instrument;
   a first tracking device associated with the instrument and operable with the coil array to at least one of transmit the second field to the array, receive the first field from the array, or combinations thereof;
   a coil array controller and navigation probe interface (CAC/NPI) system operable to control the at least three separate coils of the coil array and has a digital amplifier and a digital switch operable to switch a signal from the digital amplifier to each of the three separate coils according to the selected transmission type, and further has amplifiers, filters, and buffers to directly interface with the first tracking device;
   a single container enclosure that contains the coil array controller and navigation probe interface system;
   a display device configured with the single container to be included therewith;
   wherein the display is operable to display a tracked position of the instrument via the first tracking device transmitting location information via a transmission system to the coil array controller;
   wherein the digital switch is operable to switch a drive current from the digital amplifier to each of the at least three coils to determine a position of the first tracking device associated with the instrument;
   wherein the single container is configured to be carried by a single person and has a volume of about 32 cm$^3$ to about 9850 cm$^3$ and a mass including contents of about 2 kg to about 10 kg.

2. The navigation system of claim 1, further comprising:
   a digital power supply operable to provide an isolation between the tracking device or instrument and the patient.

3. The navigation system of claim 1, further comprising:
   a second tracking device; and
   a mounting member operable to mount the second tracking device to the patient.

4. The navigation system of claim 1, wherein the digital switch includes a MOSFET switch.

5. The navigation system of claim 4, wherein the digital amplifier includes at least three digital amplifiers wherein each of the at least three digital amplifiers is operable to drive each of the three coils in the coil array from different signals;
   wherein the coil array includes a plurality of coil arrays;
   wherein the digital switch is operable to switch a signal from each of the at least three digital amplifiers between each of the three coils in each of the plurality of coil arrays to separately drive each of the three coils in each of the plurality of coil arrays based on the different source signals.

6. The navigation system of claim 5, further comprising:
a first processor associated with the CAC/NPI to execute instructions to determine at least one of an X component, a Y component, a Z component, or combinations thereof of a position of the tracking device associated with the instrument.

7. The navigation system of claim 6, further comprising:
a second processor operable to determine a position of the determined X, Y, and Z components relative to an image data of the patient.

8. The navigation system of claim 7, further comprising:
wherein the first processor and the second processor are a single processor of the navigation system;
wherein the single processor and the display device are also included in the single container and operable as a single system to control the coil array, interface with the tracking device, and determine the position of the tracking device.

9. The navigation system of claim 3, wherein the transmission system is a wire transmission system, a wireless transmission system, or combinations thereof.

10. The navigation system of claim 9, wherein the wireless transmission system includes a channel hopping wireless communication system, a spread spectrum wireless communication system, or combinations thereof.

11. The navigation system of claim 1, further comprising:
a mounting member projecting from the single container of the coil array controller and the navigation probe interface to mount the single container to a surgical bed and carry the single container.

12. The navigation system of claim 1, further comprising:
a coil array memory system;
wherein the coil array memory system is associated with the coil array to transmit selected information to the CAC/NPI.

13. The navigation system of claim 1, further comprising:
a memory system;
wherein the memory system includes at least one of an image data, a diagnostic instruction, a navigation instruction, or combinations thereof.

14. The navigation system of claim 13, further comprising:
a processor, wherein the processor is operable to execute the diagnostic instruction stored in the memory system to assist in determining an operability of the CAC/NPI.

15. A navigation system for use in an operating theater to navigate a procedure relative to a patient comprising:
an imaging device to obtain image data of the patient;
a surgical instrument to assist in performing a surgical procedure on the patient;
a tracking system including:
a tracking device interconnected with the surgical instrument;
a plurality of tracking arrays; and
a system controller including:
a tracking array controller having:
a digital power source operable to digitally control an alternating current power supply to the tracking array controller,
a first circuit board,
a drive system included on the first circuit board and including a digital amplifier to amplify the current from the digital power source to drive each of the tracking arrays,
a D/A converter on the first circuit board, and
a digital MOSFET switch on the first circuit board; and
a tracking device interface powered via the digital power source and having amplifiers, filters, and buffers to directly interface with the tracking device;
wherein each of the plurality of tracking arrays include at least one coil operable to be driven by an amplified current from the digital amplifier to produce an electromagnetic field relative to the patient;
wherein the tracking device includes an electromagnetic field sensitive element operable to sense the electromagnetic field produced by the at least one coil;
wherein the digital MOSFET switch is operable to switch the current from the digital amplifier between the at least one coil of each of the plurality of the tracking arrays; and
a single container enclosure that contains the system controller including the tracking array controller and the tracking device interface.

16. The navigation system of claim 15, wherein the tracking system further comprises:
a processor system including a memory and a processor operable to execute instructions stored in the memory to determine at least one of an X component, a Y component, a Z component, or combinations of the components of a position of the tracking device in space relative to the patient and to determine the position of the tracking device relative to the image data based upon the determined at least one of the X component, Y component, Z component, or combinations of the components of the position of the tracking device;
wherein the processor system and the tracking system are fixed in a single container.

17. The navigation system of claim 15, wherein the tracking array controller includes a processor operable to execute instructions;
wherein the tracking device interface is interconnected with the tracking device to communicate information regarding the tracking device in the field produced by the tracking array to be processed by the processor;
wherein the processor is operable to execute instructions to determine at least one of an X component, a Y component, a Z component, or combinations thereof components of a position of the tracking device in space relative to the patient.

18. The navigation system of claim 17,
wherein the processor is operable to determine the position of the tracking device relative to the image data based upon the determined X component, Y component, Z component, or combinations of the components of the position of the tracking device.

19. The navigation system of claim 18, further comprising:
a display operable to display a representation of the position of the surgical instrument relative to the image data based upon the determined position component of the tracking device.

20. The navigation system of claim 15, further comprising:
a wireless transmission system operable to transmit a signal from the tracking device to the tracking array controller.

21. The navigation system of claim 15, wherein the tracking array controller includes a processor and a memory system;

wherein the memory system includes a diagnostic program operable to be executed by the processor to determine appropriate operation of the tracking array controller, the tracking array, the digital amplifier, or combinations thereof.

22. The navigation system of claim 15, wherein the digital amplifier includes a plurality of digital amplifiers, and the digital MOSFET switch includes a plurality of digital MOSFET switches;
wherein each of the plurality of digital amplifiers is interconnected with each of the plurality of the tracking arrays through at least one of the plurality of digital MOSFET switches to allow switching of a current from each of the plurality of digital amplifiers to selectively power each one of the plurality of the tracking arrays.

23. The navigation system of claim 22,
wherein each of the plurality of tracking arrays includes a plurality of coils;
wherein the plurality of digital MOSFET switches is operable to switch a drive current from one of each of the plurality of coils in one of the plurality of the tracking arrays to another of each of the plurality of coils in another of the plurality of the tracking arrays.

24. The navigation system of claim 22, wherein the CAC/NPI further comprises a first circuit board;
wherein at least the plurality of digital amplifiers and the plurality of digital MOSFET switches are connected to the first circuit board.

25. The navigation system of claim 24, wherein the CAC/NPI further comprises a digital power source.

26. The navigation system of claim 22, wherein the single container is configured to be carried by a single person and has a volume of about 32 cm$^3$ to about 9850 cm$^3$ and a mass including contents of about 2 kg to about 10 kg.

27. A navigation system for use in an operating theater to navigate a procedure relative to a patient, comprising:
a container operable to be carried and transported by a single user enclosing a volume of about 32 cc to about 9850 cc, wherein the container contains at least a tracking array controller having at least one digital switch and at least one digital amplifier, a navigation probe interface, and the container encloses a space to contain a tracking array;
wherein the tracking array controller can power and control a plurality of coils of a tracking array using the at least one digital switch and the at least one digital amplifier,
wherein the tracking array controller can control the tracking array to determine a location of a tracking device to be displayed on a display,
wherein the navigation probe interface includes an input receiving interface for a tracking device,
wherein the tracking array includes a plurality of tracking coils, the at least one digital amplifier includes a plurality of digital amplifiers, and the at least one digital switch includes a plurality of digital switches;
wherein each of the plurality of digital amplifiers is interconnected with each of the plurality of the tracking coils through at least one of the plurality of digital switches to allow switching of a current from each of the plurality of digital amplifiers to selectively power each one of the plurality of the tracking coils.

28. The navigation system of claim 27, further comprising:
a tracking device including a coil to at least one of transmit a field and receive a field; and
the plurality of coils positioned relative to one another and each of the coils driven through the at least one digital amplifier;
wherein the tracking array is operable to at least one of transmit a field and receive a field relative to the tracking device.

29. The navigation system of claim 28,
wherein the tracking array includes a plurality of tracking arrays, wherein each of the tracking arrays includes a plurality of coils;
wherein the plurality of digital switches are operable to switch a drive current from one of each of the plurality of coils in one of the plurality of the tracking arrays to another of each of the plurality of coils in another of the plurality of the tracking arrays.

30. The navigation system of claim 29, wherein the tracking device is operable to be influenced by a field produced by the tracking array and produce a signal based upon an induced voltage from the field produced by the tracking array.

31. The navigation system of claim 30, wherein the tracking array controller includes a processor operable to execute instructions to determine a position component of the tracking device based upon the induced voltage.

32. The navigation system of claim 31,
wherein the display is operable to display the determined position component of the tracking device.

33. The navigation system of claim 32, further comprising:
a processor operable to execute instructions to determine a position of the tracking device relative to an image data of the patient;
wherein the determined position of the tracking device can be displayed relative to the image data.

34. The navigation system of claim 33, further comprising:
a surgical instrument;
wherein the tracking device is operably associated with the instrument to determine a position of the instrument;
wherein a representation of the instrument is operable to be displayed on the display relative to the image data.

35. The navigation system of claim 28, further comprising:
a communications system wherein the tracking device is operable to communicate to the tracking array controller a signal.

36. The navigation system of claim 35, wherein the communication system is a wireless communications system.

37. The navigation system of claim 28,
wherein each of the plurality of digital switches is a digital MOSFET switch;
wherein the digital MOSFET switch is operable to control a drive current from each of the plurality of digital amplifiers to each of the plurality of the tracking arrays.

38. The navigation system of claim 27, further comprising:
at least one of a navigation processor and an image processor; and
a wireless communication system operable to transmit data between the navigation processor, the image processor, the tracking array controller, the navigation probe interface, or combinations thereof.

39. The navigation system of claim 5, wherein the digital amplifier includes a plurality of digital amplifiers, and the digital MOSFET switch includes a plurality of digital MOSFET switches;
wherein each of the plurality of digital amplifiers is interconnected with each of the plurality of the tracking arrays through at least one of the plurality of digital MOSFET switches to allow switching of a current from each of the plurality of digital amplifiers to selectively power each one of the plurality of the tracking arrays.

40. The system of claim 39, wherein the single container includes at least two dimensions of about 1.5 feet by about six inches.

41. A method of navigating an instrument relative to a patient with a navigation system in an operating theater, comprising:

transporting by a single user a single container enclosing a volume of about 32 cc to about 9850 cc, wherein the single container contains at least a tracking array controller and navigation probe interface system (TAC/NPI) having a plurality of digital switches and a plurality of digital amplifiers, and the container encloses a space to contain a tracking array;

providing in the container a first circuit board to which is fixed a digital power source operable to digitally control an alternating current power supply to the TAC/NPI, a drive system including the plurality of digital amplifiers to amplify the current from the digital power source to drive a plurality of tracking arrays, a D/A converter, and the plurality of a digital switches;

powering and controlling a plurality of coils of the plurality of tracking arrays using the plurality of digital switches and the plurality of digital amplifiers of the TAC/NPI;

at least one of transmitting a field and receiving a field with a tracking device having a coil, wherein each of the plurality of tracking arrays are operable to at least one of transmit a field and receive a field relative to the tracking device;

determining a location of a tracking device to be displayed on a display at least by executing instructions with a processor included in the container;

wherein each of the plurality of digital amplifiers is interconnected with each of the plurality of the tracking arrays through at least one of the plurality of digital switches to allow switching of a current from each of the plurality of digital amplifiers to selectively power each one of the plurality of the tracking arrays;

wherein the plurality of digital switches are operable to switch a drive current from one of each of the plurality of coils in one of the plurality of the tracking arrays to another of each of the plurality of coils in another of the plurality of the tracking arrays.

42. The method of claim 41, further comprising producing a signal with the tracking device based upon an induced voltage from the field produced by at least one of the plurality of the tracking arrays.

* * * * *

UNITED STATES PATENT AND TRADEMARK OFFICE
CERTIFICATE OF CORRECTION

PATENT NO. : 8,320,991 B2
APPLICATION NO. : 11/607762
DATED : November 27, 2012
INVENTOR(S) : Jascob et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this
Second Day of December, 2014

Michelle K. Lee
*Deputy Director of the United States Patent and Trademark Office*